United States Patent
Breakspear et al.

(10) Patent No.: US 12,296,034 B2
(45) Date of Patent: May 13, 2025

(54) RESHAPING COMPOSITION FOR KERATIN FIBERS

(71) Applicant: KAO GERMANY GMBH, Darmstadt (DE)

(72) Inventors: Steven Breakspear, Darmstadt (DE); Niu Jian, Darmstadt (DE); Bernd Nöcker, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 423 days.

(21) Appl. No.: 17/788,517

(22) PCT Filed: Feb. 23, 2021

(86) PCT No.: PCT/EP2021/054416
§ 371 (c)(1),
(2) Date: Jun. 23, 2022

(87) PCT Pub. No.: WO2021/170568
PCT Pub. Date: Sep. 2, 2021

(65) Prior Publication Data
US 2023/0039316 A1    Feb. 9, 2023

(30) Foreign Application Priority Data

Feb. 28, 2020 (EP) .................... 20159952

(51) Int. Cl.
| | |
|---|---|
| *A61K 8/41* | (2006.01) |
| *A45D 7/06* | (2006.01) |
| *A61K 8/37* | (2006.01) |
| *A61K 8/60* | (2006.01) |
| *A61K 8/73* | (2006.01) |
| *A61K 8/81* | (2006.01) |
| *A61Q 5/06* | (2006.01) |

(52) U.S. Cl.
CPC ............. *A61K 8/41* (2013.01); *A45D 7/06* (2013.01); *A61K 8/37* (2013.01); *A61K 8/604* (2013.01); *A61K 8/73* (2013.01); *A61K 8/8117* (2013.01); *A61K 8/8147* (2013.01); *A61Q 5/06* (2013.01); *A61K 2800/48* (2013.01)

(58) Field of Classification Search
CPC . A61K 8/41; A61K 8/604; A61K 8/73; A61K 8/8117; A61K 8/8147; A61K 2800/48; A45D 7/06; A61Q 5/06
See application file for complete search history.

(56) References Cited

U.S. PATENT DOCUMENTS

2009/0010855 A1    1/2009  Lepilleur et al.
2018/0015015 A1 *  1/2018  Pressly ............... A61Q 5/04

FOREIGN PATENT DOCUMENTS

| CN | 1260708 A | 7/2000 | |
|---|---|---|---|
| WO | 98/52517 A1 | 11/1998 | |
| WO | WO-0238114 A1 * | 5/2002 | ........... A61K 8/41 |
| WO | 2016/098870 A1 | 6/2016 | |
| WO | WO-2016182086 A1 * | 11/2016 | ........... A61K 8/44 |
| WO | 2019/074129 A1 | 4/2019 | |

OTHER PUBLICATIONS

Bates, R.G., et al. (1949) Dissociation Constants of Weak Bases from Electromotive-Force Measurements of Solutions of Partially Hydrolyzed Salts, J. Res. Natl. Bur. Std. 43, p. 519-526 (Year: 1949).*
Tinto, W.F. et al. (2017). Chapter 22—Waxes, Pharmacognosy, Academic Press. pp. 443-455. (Year: 2017).*
International Search Report issued Mar. 25, 2021, in connection with PCT International Application No. PCT/EP2021/054416.
PCT Written Opinion in connection with PCT International Application No. PCT/EP2021/054416.
English-language machine-generated translation of Chinese Office Action mailed Jul. 29, 2023, in connection with counterpart Chinese Application No. 202180015424.3.

* cited by examiner

*Primary Examiner* — Sue X Liu
*Assistant Examiner* — Susannah S Armstrong
(74) *Attorney, Agent, or Firm* — Norris McLaughlin, P.A.

(57) ABSTRACT

Reshaping compositions, methods or processes, and kits-of-part reshape keratin fibers. The reshaping composition is a non-reducing, non-oxidizing composition for keratin fibers having a pH in the range of 7 to 12, and comprising a) one or more organic alkalizing agents having a $pK_a$ of less than 9.0, b) one or more lipophilic compounds being liquid at 25° C. and atmospheric pressure, at a total concentration in the range of 10% to 80% by weight, calculated to a total weight of the composition, c) one or more surfactants, and d) one or more thickening agents.

19 Claims, No Drawings

RESHAPING COMPOSITION FOR KERATIN FIBERS

This application is the U.S. National Stage of International Application No. PCT/EP2021/054416, filed Feb. 23, 2021, which claims foreign priority benefits under 35 U.S.C. § 119 of European Application No. 20159952.9, filed Feb. 28, 2020, the disclosures of which are incorporated herein by reference.

FIELD OF THE INVENTION

The present invention is directed to a reshaping composition for keratin fibers, a reshaping process, and kit-of-parts.

BACKGROUND OF THE INVENTION

Current permanent reshaping processes require steps of reducing the hair and later oxidizing the hair. The reducing step employs reducing agents, such as thioglycolic acid, in order to cleave disulphide bonds within the hair and to allow protein chain movement. In a subsequent step the bonds are reformed by addition of an oxidizing composition, typically comprising hydrogen peroxide. In Western countries these well known processes include cold perming and hot perming techniques, whereas, especially in Asian countries, a digital perming as a specialty of the hot perming process is preferred. For a digital perming process the temperature of the perm is controlled by an electronic device, often being equipped with a microprocessor. These multi-step processes are time-consuming (up to 3 hours for a cold perm/5 hours for a digital perm), require a high level of winding skill from the stylist, cause hair damage and, at worst, can lead to hair loss due to over-processing. Over-processing typically stems from either leaving the reducing agent for too long on the hair, or heating the hair to inappropriate temperatures for a too long time. To avoid over-processing, a test curler is typically carried out on a streak of the client's hair prior to the full process being performed, in order to determine the optimum processing time; this adds further to the time needed and requires further skills/education from the stylist. Apart from all the process challenges, the reducing composition has a strong and acrid odour disliked by stylists and consumers alike.

For easing the application of reshaping compositions, WO2016/098870 discloses alkaline non-reducing, non-oxidizing compositions comprising fatty compounds and water-soluble thickening polymers.

SUMMARY OF THE INVENTION

The first object of the present invention is a non-reducing, non-oxidizing reshaping composition for keratin fibers, preferably human keratin fibers, more preferably human hair, having a pH in the range of 7 to 12, and comprising:
  a) one or more organic alkalizing agent(s) having a $pK_a$ of less than 9.0,
  b) one or more lipophilic compound(s) being liquid at 25° C. and atmospheric pressure, at a total concentration in the range of 10% to 80% by weight, calculated to the total weight of the composition,
  c) one or more surfactant(s),
  d) one or more thickening agent(s).

The reshaping composition of the present invention may optionally comprise one or more organic and/or inorganic alkalizing agent having a $pK_a$ of 9.0 or more as compound(s) according to e).

The second object of the present invention is a process for reshaping keratin fibers, preferably human keratin fibers, more preferably human hair comprising the steps of:
  i) putting keratin fibers under mechanical tension,
  ii) applying to keratin fibers the composition as defined above,
  iii) optionally covering keratin fibers with a moisture barrier,
  iv) heating the keratin fibers to a temperature in the range of 50° C. to 230° C.,
  v) optionally removing the moisture barrier from keratin fibers,
  vi) releasing tension from keratin fibers,
  vii) optionally rinsing-off the keratin fibers,
  wherein process steps i), ii), and vi), vii) can be executed in either order.

The third object of the present invention is a kit-of-parts comprising the composition as defined above and one or more digital perm curler(s).

DETAILED DESCRIPTION OF THE INVENTION

Inventors of the present invention have unexpectedly found out that alkaline non-reducing, non-oxidizing compositions comprising an organic alkalizing agent having a $pK_a$ below a certain threshold, lipophilic compound, surfactant, and thickening agent improve curling efficiency during perming, improve cosmetic safety by preventing dripping at process temperatures above 80° C., and improve the cosmetic properties of keratin fibers such as feel, touch, and shine. Moreover, the composition has less to no odor and may be applied without having to cover the keratin fibers with a moisture barrier.

Reshaping Composition

The present invention is directed to a non-reducing, non-oxidizing reshaping composition for keratin fibers, preferably human keratin fibers, more preferably human hair, having a pH in the range of 7 to 12, and comprising:
  a) one or more organic alkalizing agent(s) having a $pK_a$ of less than 9.0,
  b) one or more lipophilic compound(s) being liquid at 25° C. and atmospheric pressure, at a total concentration in the range of 10% to 80% by weight, calculated to the total weight of the composition,
  c) one or more surfactant(s),
  d) one or more thickening agent(s).

The term 'non-reducing' within the meaning of the present invention is to be understood that the composition from above is free of agents causing a reduction of disulfide bonds in the keratin fibers. This is usually the case at concentrations of reducing agents below 1% by weight, preferably below 0.1% by weight, calculated to the total weight of the composition. Thus, the term 'non-reducing' does not exclude low amounts of reducing agents which may be necessary in the composition for stabilizing purposes. Most preferably, the composition of the present invention is free of reducing agents.

The term 'non-oxidizing' within the meaning of the present invention is to be understood that the composition from above is free of oxidizing agents causing an oxidation of disulfide bonds in the keratin fibers. This is usually the case at concentrations of oxidizing agents below 1% by weight, preferably below 0.1% by weight, calculated to the total weight of the composition. The term does not exclude low amounts of oxidizing agents, which may be necessary in the composition for stabilizing purposes. Most preferably, the composition of the present invention is free of oxidizing agents.

It is preferred from the viewpoint of reshaping performance that the composition above is a permanent waving composition.

It is further preferred from the viewpoint of reshaping durability that the composition from above is a composition for reshaping with heat above 50° C., preferably with heat of 80° C. or more.

It is preferred from the viewpoint of keratin fiber reshaping performance that the pH of the composition is 7.5 or more, more preferably 8 or more, further more preferably 8.5 or more.

It is preferred from the viewpoint of keratin fiber reshaping performance, cosmetic safety, and damage to keratin fibers that the pH of the composition is 11 or less, more preferably 10.5 or less, further more preferably 10.0 or less.

For attaining the above-mentioned effects, it is preferred that the pH of the composition is in the range of 7.5 to 11, more preferably 8 to 10.5, further more preferably 8.5 to 10.0.

It is preferred from the viewpoint of rinsability that the composition of the present invention is an aqueous composition. In this respect, it is preferred that the composition of the present invention comprises water at 15% by weight or more, more preferably at 20% by weight or more, further more preferably at 30% by weight or more, still further more preferably at 40% by weight or more, still further more preferably at 50% by weight or more, still further more preferably at 60% by weight or more, still further more preferably at 80% by weight or more, calculated to the total weight of the composition.

It is preferred from the viewpoint of keratin fibers reshaping performance that the composition of the present invention comprises water at 90% by weight or less, more preferably at 85% by weight or less, further more preferably at 75% by weight or less, calculated to the total weight of the composition.

For attaining the above-mentioned effects, it is preferred that the composition of the present invention comprises water in the range of 15% to 90% by weight, more preferably 20% to 85% by weight, further more preferably 30% to 75% by weight, still further more preferably 40% to 75% by weight, still further more preferably 50% to 75% by weight, still further more preferably 60% to 75% by weight, calculated to the total weight of the composition.

The composition of the present invention preferably is an emulsion. Depending on the concentration of compound(s) according to b), it may be presented in the form of an oil-in-water emulsion. However, at higher concentrations of compound(s) according to b), it may also be possible to formulate the composition as an inverse emulsion, i.e. a water-in-oil emulsion.

Alkalizing Agent(s) According to a)

In principle, any organic alkalizing agent(s) having a $pK_a$ of less than 9.0 is suitable for the present invention.

It is preferred from the viewpoint of keratin fiber damage that the compound(s) according to a) have/has a $pK_a$ of less than 8.5, preferably the $pK_a$ is in the range of 7 to 8.5.

Suitable examples are tris-(hydroxymethyl)-aminomethane, 2-(4-(2-Hydroxyethyl)-1-piperazinyl)-ethanesulfonic acid, triethanolamine, morpholine and morpholine derivatives, and/or their salt(s), and/or their mixtures.

It is preferred from the viewpoint of keratin fiber damage and reshaping performance that one or more organic alkalizing agent(s) having a $pK_a$ of less than 9.0 is tris(hydroxymethyl)-aminomethane.

It is preferred from the viewpoint of providing alkalinity and keratin fibers reshaping performance that the total concentration of alkalizing agent(s) in the composition of the present invention is 0.1% by weight or more, preferably 0.5% by weight or more further more preferably 1% by weight or more, still more preferably 2% by weight or more, calculated to the total weight of the composition.

It is preferred from the viewpoint of keratin fibers reshaping performance and cosmetic safety that the total concentration of alkalizing agent(s) in the composition of the present invention is 15% by weight or less, preferably 10% by weight or less further more preferably 8% by weight or less, calculated to the total weight of the composition.

For attaining the above-mentioned effects, it is preferred that the total concentration of alkalizing agent(s) of the composition of the present invention is in the range of 0.1% to 15% by weight, preferably in the range of 0.5% to 10% by weight, more preferably in the range of 1% to 8% by weight, still more preferably in the range of 2% to 8% by weight, calculated to the total weight of the composition.

Lipophilic Compounds According to b)

The composition of the present invention comprises one or more lipophilic compound(s) being liquid at 25° C. and atmospheric pressure, at a total concentration in the range of 10% to 80% by weight, calculated to the total weight of the composition, as compound(s) according to b).

It is preferred from the viewpoint of composition stability that the compound(s) according to b) are selected from natural and/or vegetable oils, mineral oil, and fatty acid esters consisting of linear or branched, saturated or unsaturated fatty acids with $C_{12}$ to $C_{22}$ being esterified with linear or branched primary alcohols with $C_3$ to $C_{12}$, silicones, lauryl alcohol, and/or their mixtures.

Suitable natural and/or vegetable oils are, for example, olive oil, sunflower oil, rapeseed oil, wheatgerm oil, or almond oil.

Suitable silicones are, for example, linear or cyclic silicones with or without amination, such as dimethicone, trimethicone, and/or amodimethicone.

The preferred compound(s) according to b) are selected from fatty acid esters consisting of linear or branched, saturated or unsaturated fatty acids with $C_{12}$ to $C_{22}$ being esterified with linear or branched primary alcohols with $C_3$ to $C_{12}$, more preferably they are selected from isopropyl palmitate, octyl palmitate, isocetyl palmitate, octyl stearate, oleyl oleate, myristyl myristate, and/or their mixtures, form the viewpoint of curling efficiency and composition stability. The most preferred compound according to b) is isopropyl myristate, from the viewpoint of keratin fiber reshaping, removability with washing, and composition stability.

It is preferred from the viewpoint of keratin fibers reshaping performance that the total concentration of compound(s) according to b) is 15% by weight or more, more preferably 20% by weight or more, further more preferably 25% by weight or more, calculated to the total weight of the composition.

It is preferred from the viewpoint of removability with washing and composition stability that the total concentration of compound(s) according to b) is 75% by weight or less, more preferably 70% by weight or less, further more preferably 60% by weight or less, still further more preferably 50% by weight or less, still further more preferably 40% by weight or less, calculated to the total weight of the composition.

For attaining the above-mentioned effect, it is preferred that the total concentration of compound(s) according to b) is in the range of 15% to 75% by weight, preferably 20% to 70% by weight, more preferably 25% to 60% by weight, further more preferably 25% to 50% by weight, still further more preferably 25% to 40% by weight, calculated to the total weight of the composition.

Compounds According to c)

The composition of the present invention comprises one or more surfactant(s) as compound according to c).

It is preferred from the viewpoint of composition stability that the compound(s) according to c) are selected from anionic, non-ionic, amphoteric and/or zwitterionic, and/or cationic surfactants, and/or their mixtures.

Suitable anionic surfactants are selected from ethoxylated or non-ethoxylated alkyl ether sulfate surfactants, alkyl sulfates, ethoxylated and/or non-ethoxylated alkyl carboxylates, ethoxylated or non-ethoxylated amino acid surfactants, and/or their mixtures.

Suitable alkyl sulfate or preferably ethoxylated alkyl ether sulfate surfactant or mixtures thereof have an alkyl chain length of $C_{10}$ to $C_{22}$.

Suitable example anionic surfactants are laureth sulfates, coceth sulfate, pareth sulfate, capryleth sulphate, myreth sulfate, oleth sulfate, deceth sulfate, trideceth sulfate, coco sulphate, $C_{10}$-$C_{16}$ alkyl sulphate, $C_{11}$-$C_{15}$ alkyl sulphate, $C_{12}$-$C_{18}$ alkyl sulphate, $C_{12}$-$C_{15}$ alkyl sulphate, $C_{12}$-$C_{16}$ alkyl sulphate, $C_{12}$-$C_{13}$ alkyl sulfate, lauryl sulphate, myristyl sulphate, palm kernel sulphate, cetearyl sulfate, cetyl sulphate, decyl sulphate, oleyl sulphate, behenyl sulphate and/or their salts. All of the aforementioned anionic surfactants may or may not be ethoxylated at various degrees.

Cations for the surfactants may be selected from sodium, potassium, magnesium and/or ammonium.

Suitable non-ionic surfactants are alkyl polyglycosides, ethoxylated triglycerides, ethoxylated fatty alcohols, ethoxylated fatty acid esters, and/or their mixtures.

Preferred non-ionic surfactants are alkyl polyglycosides according to the general structure:

$$R_{23}O(R_{24}O)_tZ_x$$

Wherein Z denotes a carbohydrate with $C_5$ to $C_6$, $R_{23}$ is an alkyl group with $C_8$ to $C_{18}$, $R_{24}$ is methyl, ethyl or propyl, t ranges from 0 to 10, and x ranges from 1 to 5. Suitable compounds according to this structure are $C_9$-$C_{11}$ alkylpolyglycoside, the structures disclosed in EP-A 70 074, and JP 2015-123019A.

The most preferred compounds according to the structure of above are decyl glucoside, lauryl glucoside, and coco glucoside.

Suitable amphoteric/zwitterionic surfactants are compounds according to the general structure(s)

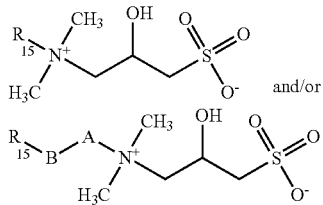

and/or wherein $R_{15}$ is a straight or branched, saturated or unsaturated, substituted or unsubstituted alkyl chain with a carbon number of $C_{10}$ to $C_{22}$, preferably $R_{15}$ is a straight alkyl chain with a carbon number of $C_{10}$ to $C_{16}$, A is a straight alkyl chain with a carbon number of $C_1$ to $C_6$ or a branched alkyl chain with a carbon number of $C_3$ to $C_6$, preferably A is a linear alkyl chain with a carbon number of $C_3$, and B is an amide or an ester group.

Suitable compounds are known as hydroxysultaine surfactants, such as cocoamidopropyl hydroxysultaine, laurylamidopropyl hydroxysultaine, erucamidopropyl hydroxysultaine, lauryl hydroxysultaine, and cocoyl hydroxysultaine, and/or their salt(s).

Further suitable amphoteric/zwitterionic surfactants are of betaine type. Suitable compounds may be selected from alkyl betaines and/or alkylamido betaines. A preferred compound selected from alkyl betaines is lauryl betaine. A preferred compound selected from alkylamido betaines is cocamidopropyl betaine. The disclosure also relates to the salts of the compounds.

The preferred amphoteric/zwitterionic surfactant(s) is/are selected from alkylamido betaines and/or alkylamidoalkyl betaine surfactants.

Suitable cationic surfactants are of quaternary ammonium structure according to the following general structure

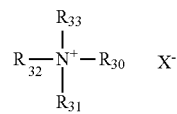

where $R_{30}$ is a saturated or unsaturated, branched or linear alkyl chain with $C_8$-$C_{22}$ or

where $R_{34}$ is saturated or unsaturated, branched or linear alkyl chain with $C_7$-$C_{21}$ atoms and n has typical value of 1-4 or

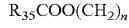

where $R_{35}$ is saturated or unsaturated, branched or linear alkyl chain with $C_7$-$C_{21}$ atoms and n has typical value of 1-4, and $R_{31}$ is unsaturated or saturated, branched or linear alkyl chain with $C_1$-$C_{22}$ atoms or

or

where $R_{34}$, $R_{35}$ and n are same as above.

$R_{32}$ and $R_{33}$ have an alkyl chain with $C_1$ to $C_4$, and $X^-$ typically is chloride, bromide, or methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimethyl ammonium chloride, dioleoylethyl dimethyl ammonium methosulfate, dioleoylethyl hydroxyethylmonium methosulfate, behenyl trimethyl ammonium chloride, and/or their mixtures.

It is preferred from the viewpoint of composition stability that the total concentration of compound(s) according to c) is 0.1% by weight or more, preferably 0.5% by weight or more, further more preferably 0.75% by weight or more, calculated to the total weight of the composition.

It is preferred from the viewpoint of composition stability and cost of goods that the that the total concentration of compound(s) according to c) is 10% by weight or less, further more preferably 7% by weight or less, still further more preferably 5% by weight or less, calculated to the total weight of the composition.

For attaining the above-mentioned effects, it is preferred that the total concentration of compound(s) according to c) is in the range of 0.1% to 10% by weight, preferably 0.5% to 7% by weight, more preferably in the range of 0.75% to 5% by weight, calculated to the total weight of the composition.

Thickening Agent as Compounds According to d)

The composition of the present invention comprises one or more thickening agent(s).

It is preferred from the viewpoint of composition stability that the compound(s) according to d) is/are a thickening polymer, preferably a non-ionic, anionic, non-ionic, and/or cationic thickening polymer, more preferably an anionic thickening polymer.

Suitable anionic thickening polymers are copolymers and/or crosspolymers which comprise an acrylate and/or methacrylate monomer unit and optionally least one more hydrophobic unit such as alkyl chains. Examples are acrylates/c10-30 alkyl acrylate crosspolymer, acrylates/steareth-20 methacrylate copolymer, acrylates/stearyl acrylate/dimethicone methacrylate copolymer, acrylates/beheneth-25 methacrylate copolymer, acrylates/lauryl acrylate/stearyl acrylate/ethylamine oxide methacrylate copolymer, carboxymethyl cellulose, alginic acids, sodium alginates, ammonium alginates, calcium alginates, gum arabic, guar gum or xanthan gum, dehydroxanthan gum or acrylic acid polymers known with the CTFA adopted name Carbomer and its derivatives.

Suitable non-ionic thickening polymers are, for example, alkyl modified cellulose derivatives such as ($C_2$-$C_8$)-alkylcellulose, cellulose polymers, preferably methyl cellulose, ethyl cellulose, hydroxyethylcellulose, methylhydroxyethylcellulose, methylhydroxypropylcellulose, or starch based polymers such as vegetable starch and/or their synthetically modified derivatives such as hydroxypropyl starch phosphate.

Suitable cationic non-associative polymers are Polyquaternium 6, Polyquaternium 16, and Polyquaternium 37.

The most preferred thickening polymers of the composition of the present invention are Carbomer and xanthan gum.

In one aspect of the present invention the one or more thickening agent(s) according to d) is/are thickening agents being soluble in or mixable with the compounds according to b).

The term 'soluble' within the meaning of the present invention denotes the that the compounds according to d) may be solid at 25° C. and atmospheric pressure, but are able to completely dissolve in the compounds according to b). Preferably, the complete dissolution appears at 25° C. under atmospheric pressure. However, for the purpose of the present invention, it is sufficient that the thickening agent according to d) dissolves in the compounds according to b) at elevated temperatures leading to sufficient thickening of the composition at these temperatures, for example at process temperatures of keratin fiber treatment at 80° C. Hence, it is not required that at 25° C. and atmospheric pressure a complete solution of the compounds according to d) is possible to obtain.

The term 'mixable' denotes that the compounds according to d) may be liquid at 25° C. and atmospheric pressure. Hence, the compounds according to d) must be at least partially mixable with the compounds according to b) at 25° C. under atmospheric pressure. However, complete mixability should be obtained at process temperatures of keratin fiber treatment at 80° C., then delivering the required thickening effect.

In one aspect of the present invention, the oil-soluble thickening agent according to d) is an oil-soluble thickening polymer, preferably a non-ionic, anionic, non-ionic, and/or cationic oil-soluble thickening polymer, more preferably a non-ionic oil-soluble polymer.

Hence, it is preferred for the purpose of the present invention that the compound(s) according to d) are able to thicken the composition of the present invention at a temperature of 80° C. or more. Thus, it is preferred from the viewpoint of heat stability of the composition and keratin fiber reshaping performance that the viscosity of the composition at 80° C. is 1,000 mPas or more, more preferably 5,000 mPas or more, further more preferably 10,000 mPas or more, measured by plate-cone viscometry, for example with a Brookfield viscometer with appropriate spindle.

It is preferred from the viewpoint of manufacturing that the compounds according to d) are solid or pasty at 25° C. under atmospheric conditions.

In one aspect of the present invention, the oil-soluble thickening agent according to d) is an oil-soluble thickening polymer, preferably a non-ionic, anionic, non-ionic, and/or cationic oil-soluble thickening polymer, more preferably a non-ionic oil-soluble polymer.

It is preferred from the viewpoint of oil solubility of the thickening polymer that the compound(s) according to d) is a homopolymer or copolymer comprising monomer units of ethylene and/or propylene and/or butylene and/or styrene.

Suitable non-ionic polymers satisfying the description of above are, for example, copolymers of ethylene/butylene with styrene monomers are commercially available under the trade name Kraton polymers, for example Kraton G1701E.

In another aspect of the present invention, the compounds according to d) is/are hydrogenated vegetable oil, which is commercially available under the trade name Dermofeel Viscolid from Evonik Ind. AG.

Thus, preferred thickening agents according to d) are homopolymers or copolymers comprising monomer units of ethylene and/or propylene and/or butylene and/or styrene and hydrogenated vegetable oil, and/or their mixtures.

In another aspect of the present invention, the compounds according to d) are lipophilic compounds being solid or pasty at 25° C. under atmospheric pressure.

Suitable lipophilic compounds being solid or pasty at 25° C. under atmospheric pressure are, for example, fatty alcohols having a linear or branched, saturated or unsaturated $C_{14}$ to $C_{22}$ carbon chain, or hydrogenated oils such as hydrogenated vegetable oils.

Suitably, branched or linear, fatty alcohols having a linear or branched, saturated or unsaturated $C_{14}$ to $C_{22}$ carbon chain are myristyl alcohol, pentadecyl alcohol, cetyl alcohol, palmitoleyl alcohol, heptadecyl alcohol, stearyl alcohol, oleyl alcohol, nonadecyl alcohol, arachidyl alcohol, behenyl alcohol, and/or their mixtures. Such a mixture is cetearyl alcohol comprising stearyl alcohol and cetyl alcohol.

The most preferred thickening agents according to d) are homopolymers or copolymers comprising monomer units of ethylene and/or propylene and/or butylene and/or styrene and hydrogenated vegetable oil, and/or their mixtures.

It is preferred from the viewpoint of thickening effect and reshaping power that the total concentration of compound(s) according to d) is 0.25% by weight or more, more preferably 0.5% by weight or more, further more preferably 0.5% by weight or more, still further more preferably 1% by weight or more, calculated to the total weight of the composition.

It is preferred from the viewpoint of thickening effect, reshaping power, and product safety that the total concentration of compound(s) according to d) is 0.25% by weight or more, more preferably 0.5% by weight or more, further more preferably 1% by weight or more, calculated to the total weight of the composition.

It is preferred from the viewpoint of thickening effect, reshaping power, and rinsability of keratin fibers that the total concentration of compound(s) according to d) is 20% by weight or less, more preferably 15% by weight or less, further more preferably 12% by weight or less, calculated to the total weight of the composition.

For attaining the above-mentioned effects, it is preferred that the total concentration of compound(s) according to d) is in the range of 0.25% to 20% by weight, preferably in the range of 0.5% to 15% by weight, more preferably 1% to 12% by weight, calculated to the total weight of the composition.

Optional Compounds According to e)

The reshaping composition of the present invention may optionally comprise one or more organic and/or inorganic alkalizing agent having a $pK_a$ of 9.0 or more as compound(s) according to e).

Suitable organic alkalizing agent(s) as compound(s) according to e) are alkyl and/or alkanol amines such as mono- and/or diethanolamine, butyl ethanolamine, butyl diethanolamine, dibutyl ethanolamine, methylethanolamine, triethanolamine, N-lauryl diethanolamine, diisopropanolamine, dimethyl isopropanolamine, isopropanolamine, triisopropanolamine, isobutanolamine, and/or aminomethyl propanol. Equally suitable are salts of alkyl and/or alkanol amines with a counterion preferably selected from chloride and/or hydrogen chloride, nitrate, sulphate, phosphate, hydrogenphosphate, dihydrogenphosphate, citrate, acetate, sulphite, benzoate, salicylate.

The most preferred organic alkalizing agent(s) as compound(s) according to e) is monoethanolamine.

Suitable inorganic alkalizing agent(s) as compound(s) according to e) is/are ammonia and/or its salts.

Suitable total concentrations for compounds according to e) are in the range of 1% to 6% by weight, calculated to the total weight of the composition.

Process for Reshaping Keratin Fibers

The present invention is also directed to a process for reshaping keratin fibers, preferably human keratin fibers, more preferably human hair comprising the steps of:
i) putting keratin fibers under mechanical tension,
ii) applying to keratin fibers the composition as defined above,
iii) optionally covering keratin fibers with a moisture barrier,
iv) heating the keratin fibers to a temperature in the range of 50° C. to 230° C.,
v) optionally removing the moisture barrier from keratin fibers,
vi) releasing tension from keratin fibers,
vii) optionally rinsing-off the keratin fibers,
wherein process steps i), ii), and vi), vii) can be executed in either order.

It is preferred from the viewpoint of reshaping performance that the process is a permanent waving process.

It is preferred form the viewpoint of user convenience that for process step i) the keratin fibers are put under mechanical tension on a curler or roller having heating means. After completion of step ii) or optionally step iii), the curler may then be connected to a digital perm machine for heating the curler and the keratin fibers.

It is preferred from the viewpoint of hair reshaping performance that the keratin fibers are heated in step iv) to a temperature of 80° C. or more, more preferably to a temperature of 85° C. or more, further more preferably to a temperature of 90° C. or more.

It is preferred from the viewpoint of minimizing damage that the keratin fibers are heated in step iv) to a temperature of 180° C. or less, more preferably to a temperature of 140° C. or less, further preferably to a temperature of 120° C. or less.

For attaining the above mentioned effect, it is preferred that the keratin fibers are heated in step iv) to a temperature in the range of 80° C. to 180° C., more preferably 85° C. to 140° C., further more preferably 90° C. to 120° C.

It is further preferred from the viewpoint of processing time and speedy hair treatment that the heating time of step iv) is 2 min or more, more preferably 5 min or more, further more preferably 10 min or more, still further more preferably 20 min or more.

It is preferred from the viewpoint of keratin fiber reshaping performance and damage reduction that the heating time of step iv) is 60 min or less, more preferably 45 min or less, still further more preferably 40 min or less.

For attaining the above-mentioned effects, it is preferred that the heating time of step iv) is in the range of 2 min to 60 min, more preferably in the range of 5 min to 45 min, further more preferably in the range of 10 min to 40 min, still further more preferably 20 min to 40 min.

It is preferred from the viewpoint of keratin fiber reshaping performance that in step iii) the keratin fibers are covered with a moisture barrier. The moisture barrier of step iii) may be a foil or wrap impermeable for water vapor, or housing made of a material impermeable for water vapor, with the provision that the selected materials for the moisture barrier are heat resistant up to the selected process temperature.

In principle, many materials are suitable for serving as moisture barrier such as aluminum foil, plastic foil, and/or plastic device, which enclose the curler and/or keratin fiber streak. Alternatively, certain types of anti-flammable fabric is equally suitable. The purpose of the moisture barrier is to keep the keratin fibers moist over the total processing time of heating.

Suitable examples are re-sealable zipper storage bags made of materials such a slow density polyethylene.

For the purpose of the present invention, it is one aspect to cover the keratin fibers with the moisture barrier from the viewpoint of hair reshaping performance. In another aspect from the viewpoint of user convenience, it is preferred that the hair is not covered with a moisture barrier.

Kit-of-Parts

The present invention is also directed to a kit-of-parts comprising the composition as defined above and one or more digital perm curlers(s).

Such kit-of-parts may be offered for sale and have the advantage of user convenience, because it includes composition and devices.

It is further preferred that the kit also comprises one or more moisture barrier for covering the curler as defined in optional step ii) above.

The following examples are to illustrate the invention, but not to limit it.

EXAMPLES

Example 1

Compounds according to a) and c) were dissolved in water. Compound according to d) were separately dissolved in compound according to c). The aqueous solution was then heated to 80° C. and the oil solution was added under constant stirring. After cooling the mixture, the pH was adjusted and water balance was added.

| Compound | Ingredients | Comp. | Ex 1 | Ex 2 | Ex 3 | Ex 4 | Ex 5 | Ex6 | Ex 7 | Ex 8 | Ex 9 | Ex 10 | Ex 11 | Ex 12 |
|---|---|---|---|---|---|---|---|---|---|---|---|---|---|---|
| | | | | | | % by weight [active matter] | | | | | | | | |
| — | Monoethanolamine | 4.0 | — | — | 1.5 | 5.0 | — | — | — | — | — | — | — | — |
| a) | Tris-(hydroxymethyl)-aminomethane | — | 8.0 | 2.0 | 5.0 | 1.0 | 8.0 | 8.0 | 8.0 | 8.0 | 8.0 | 8.0 | 8.0 | — |
| a) | 4-(2-hydroxyethyl)-1-piperazinethanesulfonic acid | — | — | — | — | — | — | — | — | — | — | — | — | 15.7 |
| b) | Isopropyl myristate | 25.0 | 25.0 | 25.0 | 25.0 | 25.0 | 25.0 | 10.0 | 65.0 | 25.0 | 25.0 | 25.0 | 25.0 | 25 |

-continued

| Compound | Ingredients | Comp. | Ex 1 | Ex 2 | Ex 3 | Ex 4 | Ex 5 | Ex6 | Ex 7 | Ex 8 | Ex 9 | Ex 10 | Ex 11 | Ex 12 |
|---|---|---|---|---|---|---|---|---|---|---|---|---|---|---|
| | | | | | | % by weight [active matter] | | | | | | | | |
| c) | Coco glucoside* | 5.0 | 5.0 | 5.0 | 5.0 | 5.0 | 5.0 | 5.0 | 5.0 | 5.0 | 3.5 | 5.0 | 5.0 | 5.0 |
| d) | Carbopol 10** | 1.0 | 1.0 | 1.0 | 1.0 | 1.0 | — | 1.0 | 1.0 | 0.1 | 1.0 | — | — | 1.0 |
| d) | Xanthan gum | — | — | — | — | — | 1.0 | — | — | — | — | — | — | — |
| d) | Hydrogenated vegetable oil*** | — | — | — | — | — | — | — | — | — | — | 8.0 | — | — |
| d) | Styrene ethylene/propylene copolymer***** | — | — | — | — | — | — | — | — | — | — | — | 1.0 | — |
| pH | NaOH/HCl | | | | | | Ad 9.4 | | | | | | | |
| Balance | Water | | | | | | Ad 100.0 | | | | | | | |

*Plantacare 818 sold by BASF Corp.
**Carbopol Ultrez 10 sold by Lubrizol Corp.
***Dermofeel viscolid sold by Evonik Ind. AG
**** Kraton G1701E sold by Kraton Polymers LLC Human hair streaks (Caucasian, 21 cm long, 2 g per bundle) were purchased from Fischbach+Miller Haar, Laupheim, Germany. The hair streaks were shampooed with a commercially available shampoo under the brand name Goldwell Deep Cleansing Shampoo. Then the streaks were towel dried. Then 1 g of the compositions from above was applied to the hair streaks with a brush. The streaks were then wound on perming rods possessing an electrical heating system. The rods were then heated to a temperature in the range of 90° C. for 20 min with a digital perming machine. Then the rods were allowed to cool down, and the hair was shampooed with the same shampoo from above. The streaks were then blow-dried.

Assessment of curling efficiency was investigated by measuring and calculating the curl ratio L according to the formula:

$$L=(L_0-L_t)/L_0$$

wherein $L_0$ is the length of the hair streak prior to curling and $L_t$ is the length of the hair streak after the curling experiment. The number is reported as percentage and a higher percentage corresponds to higher curling degree.

Hair feel and hair bounce were evaluated by a panel of 10 trained experts who were asked to touch the hair after processing and to rate the feel and bounce on a scale of 1 to 4, wherein 4 indicated the strongest effect. The experts were not informed about the treatment formulation of the hair streaks. The mode value of their assessments were reported below.

The table below reports the experimental results:

| Parameter | Comp. | Ex 1 | Ex 2 | Ex 3 | Ex 4 | Ex 5 | Ex 6 | Ex 7 | Ex 8 | Ex 9 | Ex 10 | Ex 11 | Ex 12 |
|---|---|---|---|---|---|---|---|---|---|---|---|---|---|
| Curl ratio | 6.8 | 11.4 | 10.9 | 12.9 | 10.8 | 11.2 | 10.9 | 12.5 | 10.7 | 10.5 | 11.9 | 10.1 | 11.2 |
| Hair feel | + | +++ | +++ | +++ | +++ | +++ | +++ | ++ | +++ | ++ | ++ | +++ | +++ |
| Curl bounce | + | ++ | ++ | ++ | +++ | +++ | +++ | +++ | + | ++ | +++ | ++ | ++ |

Technical Effects

| Parameter | +++ | ++ | + | − |
|---|---|---|---|---|
| Hai feel | Smooth, not greasy | Smooth, slightly greasy | Slightly rough, dry | Rough |
| Curl bounce | Intense | Strong | Weak | Very weak/no bounce |

As a result it was found that the inventive compositions showed stronger curling ratios in comparison to the comparative composition. Moreover, the compositions were easy to apply and remained on the hair streak during processing. The cosmetic feel of the streaks was very good.

The following examples are within the scope of the present invention.

Example 13

| | % by weight |
|---|---|
| Tris-(hydroxymethyl)-aminomethane | 5.0 |
| Ammonia 28% | 1.0 |
| Isopropyl myristate | 25.0 |
| Coco-glucoside | 5.0 |
| Xanthan gum | 0.5 |
| Styrene ethylene/propylene copolymer | 0.5 |
| NaOH/HCl | ad pH 9.5 |
| Water | ad 100.0 |

The invention claimed is:

1. A non-reducing, non-oxidizing reshaping composition for keratin fibers, the composition having a pH in the range of 7 to 12, and comprising:
    a) one or more organic alkalizing agents having a $pK_a$ of less than 9.0;
    b) one or more lipophilic compounds being liquid at 25° C. and atmospheric pressure, at a total concentration ranging from 10% to 80% by weight, calculated to a total weight of the composition,
    c) one or more surfactants; and
    d) one or more thickening agents
    wherein the one or more organic alkalizing agents according to a) is tris-(hydroxymethyl)-aminomethane and/or a salt thereof.

2. The composition according to claim 1, wherein the pH of the composition ranges from 7.5 to 10.

3. The composition according to claim 1, wherein the one or more organic alkalizing agents according to a) have a $pK_a$ in the range of 7 to 8.5.

4. The composition according to claim 1, wherein a total concentration of the one or more alkalizing agents according to a) ranges from 0.1% to 15% by weight, calculated to the total weight of the composition.

5. The composition according to claim 1, wherein the one or more lipophilic compounds according to b) are selected from one or more natural and/or vegetable oils, and/or mineral oil, and/or fatty acid esters consisting of linear or branched, saturated or unsaturated fatty acids with $C_{12}$ to $C_{22}$ being esterified with linear or branched primary alcohols with $C_3$ to $C_{12}$, and/or silicones, and/or lauryl alcohol, and/or one or more mixtures thereof.

6. The composition according to claim 1, wherein the one or more lipophilic compounds according to b) are selected from isopropyl palmitate, octyl palmitate, isocetyl palmitate, octyl stearate, oleyl oleate, myristyl myristate, and/or one or more mixtures thereof.

7. The composition according to claim 1, wherein the one or more surfactants according to c) are selected from anionic surfactants, non-ionic surfactants, amphoteric surfactants and/or zwitterionic surfactants, and/or cationic surfactants, and/or one or more mixtures thereof.

8. The composition according to claim 1, wherein that the one or more surfactants according to c) are selected from non-ionic surfactant(s).

9. The composition according to claim 1, wherein a total concentration of the one or more surfactants according to c) ranges from 0.1% to 10% by weight, calculated to the total weight of the composition.

10. The composition according to claim 1, wherein the one or more thickening agents according to d) is/are a thickening polymer selected from a non-ionic thickening polymer, anionic thickening polymer, non-ionic thickening polymer, and/or cationic thickening polymer.

11. The composition according to claim 1, wherein the one or more thickening agents according to d) is/are selected from Carbomer and/or xanthan gum, and/or one or more mixtures thereof.

12. The composition according to claim 1, wherein the one or more thickening agents according to d) is/are lipophilic compounds being solid or pasty at 25° C. under atmospheric pressure and are mixable with the one or more lipophilic compounds according to b).

13. The composition according claim 1, wherein a total concentration of the one or more thickening agents according to d) ranges from 0.25% to 20% by weight, calculated to the total weight of the composition.

14. The composition according to claim 1, wherein the composition is a permanent waving composition.

15. The composition according to claim 1, wherein the composition is a composition for reshaping with heat above 50° C.

16. The composition according to claim 1, wherein the composition comprises water in the range of 15% to 90% by weight, calculated to the total weight of the composition.

17. A kit-of-parts comprising the composition according to claim 1 and one or more digital perm curlers.

18. A process for reshaping keratin fibers comprising:
i) putting keratin fibers under mechanical tension;
ii) applying, onto the keratin fibers, the composition according to claim 1;
iii) optionally covering the keratin fibers, with the composition applied thereto, with a moisture barrier;
iv) heating the keratin fibers to a temperature in the range of 50° C. to 230° C.;
v) optionally removing the moisture barrier from the keratin fibers;
vi) releasing tension from the keratin fibers; and
vii) optionally rinsing the composition off the keratin fibers,
wherein i) and ii), and/or vi) and vii) are executable in either order.

19. The process according to claim 18, wherein the process is a permanent waving process.

* * * * *